(12) United States Patent
Vogelsang et al.

(10) Patent No.: US 10,395,395 B2
(45) Date of Patent: Aug. 27, 2019

(54) VIRTUAL PROJECTION IMAGES FOR TOMOSYNTHESIS ARTIFACT REDUCTION

(71) Applicant: Carestream Health, Inc., Rochester, NY (US)

(72) Inventors: Levon O. Vogelsang, Webster, NY (US); Lawrence A. Ray, Rochester, NY (US); Richard A. Simon, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 78 days.

(21) Appl. No.: 15/070,042

(22) Filed: Mar. 15, 2016

(65) Prior Publication Data

US 2017/0270694 A1  Sep. 21, 2017

(51) Int. Cl.
*A61B 6/02* (2006.01)
*G06T 11/00* (2006.01)
*A61B 6/00* (2006.01)

(52) U.S. Cl.
CPC ............ *G06T 11/008* (2013.01); *A61B 6/025* (2013.01); *A61B 6/5264* (2013.01)

(58) Field of Classification Search
CPC ......... A61B 6/032; A61B 6/025; A61B 6/502; A61B 34/10; G06T 2211/412; G06T 2211/436; G06T 11/006; G06T 11/005; G06T 2211/424; G06T 11/008; G06T 2207/10112; G06T 7/0012; G06T 11/003
See application file for complete search history.

(56) References Cited

U.S. PATENT DOCUMENTS

| | | | |
|---|---|---|---|
| 6,751,284 B1 * | 6/2004 | Claus | G06T 11/005 378/21 |
| 7,664,222 B2 | 2/2010 | Jabri et al. | |
| 7,817,773 B2 * | 10/2010 | Stanton | A61B 6/466 378/15 |
| 7,965,812 B2 * | 6/2011 | Hanke | A61B 6/502 378/21 |
| 8,139,710 B2 | 3/2012 | Jabri et al. | |
| 8,259,034 B2 * | 9/2012 | Ichikawa | G06T 3/4007 345/3.3 |
| 8,305,500 B2 * | 11/2012 | Cheng | H04N 5/145 348/699 |
| 8,718,143 B2 * | 5/2014 | Chen | G06T 7/20 375/240.16 |
| 8,941,778 B2 * | 1/2015 | Hashimoto | G09G 3/3611 348/441 |

(Continued)

*Primary Examiner* — Andrew M Moyer
*Assistant Examiner* — Dennis Rosario

(57) ABSTRACT

A method for tomosynthesis volume reconstruction acquires at least a prior projection image of the subject at a first angle and a subsequent projection image of the subject at a second angle. A synthetic image corresponding to an intermediate angle between the first and second angle is generated by a repeated process of relating an area of the synthetic image to a prior patch on the prior projection image and to a subsequent patch on the subsequent projection image according to a bidirectional spatial similarity metric, wherein the prior patch and subsequent patch have n×m pixels; and combining image data from the prior patch and the subsequent patch to form a portion of the synthetic image. The generated synthetic image is displayed, stored, processed, or transmitted.

18 Claims, 14 Drawing Sheets

(56) References Cited

U.S. PATENT DOCUMENTS

| | | | | |
|---|---|---|---|---|
| 9,057,678 B2 * | 6/2015 | Lee | ................... | G01N 23/046 |
| 9,058,682 B2 * | 6/2015 | Lee | ..................... | G06T 17/00 |
| 9,384,568 B2 * | 7/2016 | Steen | ................... | G06T 5/002 |
| 2008/0285656 A1 * | 11/2008 | Au | ................... | H04N 19/563 |
| | | | | 375/240.22 |

* cited by examiner

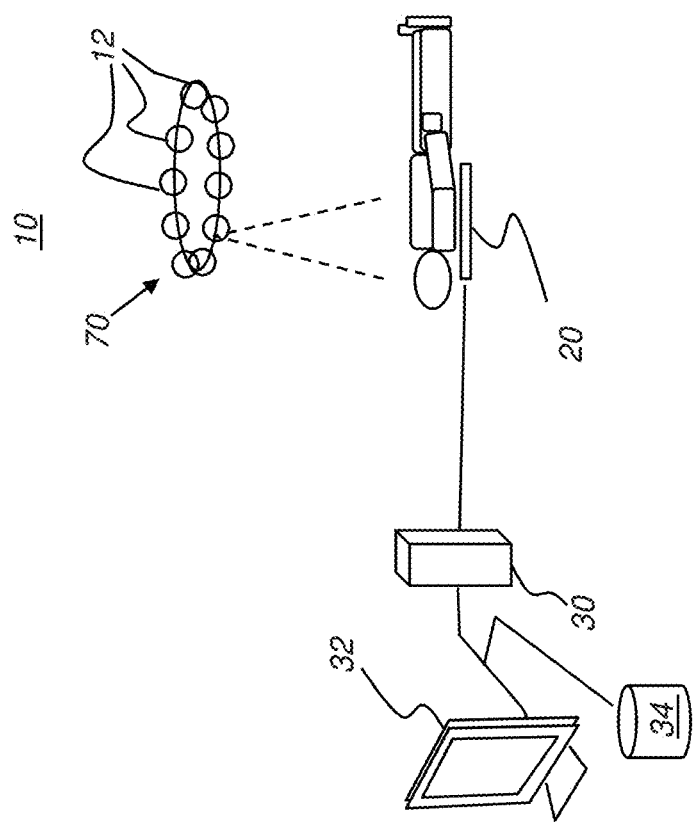

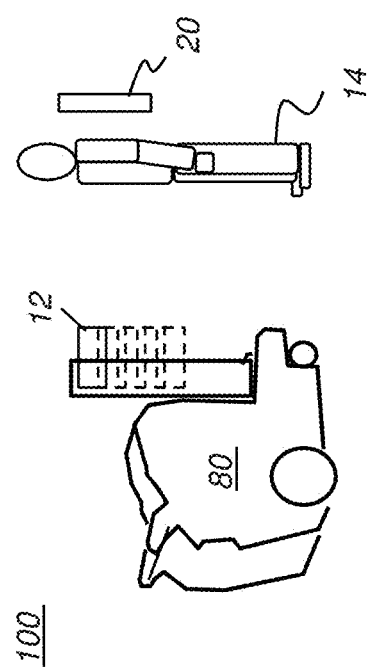

VIRTUAL PROJECTION IMAGES FOR TOMOSYNTHESIS ARTIFACT REDUCTION

FIELD OF THE INVENTION

The present disclosure relates to digital tomosynthesis imaging and more particularly to methods and apparatus for maintaining image quality while reducing the number of projection images obtained.

BACKGROUND OF THE INVENTION

Digital tomosynthesis is an imaging technique that provides three-dimensional (3D) patient images, reconstructed from a series of multiple 2D images taken over a succession of angles of the x-ray source relative to the detector. Acquisition of the 2D projection images used for tomosynthesis employs a large-area digital detector, such as a digital detector that is typically used for conventional single projection radiography.

In conventional tomosynthesis, a single X-ray source is moved along a generally linear scan path for generating multiple exposures. The set of projection image data that is acquired with tomosynthesis, by comparison, with full volume image information obtained using computed tomography (CT) or full volume imaging apparatus, is somewhat less detailed with respect to full volume information, but still allows sufficient 3D visualization for a number of diagnostic functions, at reduced exposures when compared against CT modalities. The projection images obtained for tomosynthesis, when digitally processed, yield a 3D image similar to computed tomography but with a more limited spatial resolution in the depth direction. Depth data is reconstructed from the captured projections in the form of a number of slices through the patient anatomy, with the best spatial resolution in the slices parallel to the detector plane. A consequence of limited angular scanning for tomosynthesis imaging is that the depth resolution is characteristically lower than a standard CT, but the in-plane resolution can be much higher due to the use of high resolution x-ray detectors in tomosynthesis.

The various types of tomosynthesis and tomographic imaging obtain depth information by virtue of the change of relative angle between the x-ray source and the subject for each projection image. This change is generally accomplished by movement of the x-ray source relative to the subject patient, with or without corresponding movement of the detector. The scan path of the x-ray source or detector for tomosynthesis can be linear, arcuate, or can have a planar circular arrangement. In applications where the detector is fixed, one or more movable sources may be displaced in a motion direction to vary the angle at which radiation is directed through the subject. Where an array of x-ray sources is used, the relative angle between source and detector is effectively changed by energizing successive elements of the array synchronously with image capture. Alternately, the source can remain stationary and the detector moved to different positions relative to the source and patient. Since the image is digitally generated and represented, various processing techniques can be used to generate and present a series of slices at different depths and with different thicknesses reconstructed from the same image acquisition.

Conventional tomosynthesis acquisition consists of a number of projections of X-ray exposures covering an angular range less than 180 degrees, typically 20 to 50 degrees. The patient typically stands near the detector plane during the tomosynthesis scan. The number of projections for a single wallstand scan can range from about 30 to 60. The sweep angle is the angle from the first to the final projection focal spot with respect to the focal plane.

During the scan sequence, the X-ray source is moved to different focal spot positions and a projection image for the tomosynthesis series is acquired at each position. After tomosynthesis acquisition, the digital images acquired at the detector are reconstructed into multiple image slices using a computerized reconstruction algorithm, and then viewed from an aspect in parallel to the flat panel detector face. The digital flat panel detectors developed for tomosynthesis provide rapid response, excellent dynamic range, and good quality digital images for input to the reconstruction software.

Viewing reconstructed slices is the customary and primary method of visualizing digital tomosynthesis imaging data. However, a common complication of the process of slice reconstruction is reconstruction artifacts. These artifacts result from a number of causes, particularly from an insufficient number of projections, and also due to limited angle of data acquisition and ill-posed nature of the limited view reconstruction problem.

One aspect of conventional tomosynthesis imaging is the requirement for obtaining multiple 2D projection images of the patient in order to allow 3D reconstruction. The requirement to obtain numerous images adds to the dosage levels that this imaging modality entails. In addition, this requirement also makes patient motion a problem, since some amount of motion is unavoidable for any practical exposure duration over which multiple images are obtained. Attempts to reduce the number of projection images acquired result in view artifacts in the reconstructed images, including aliasing, ripple, and other undesirable effects.

With the advent of more portable apparatus, the use of tomosynthesis imaging in clinical environments is expected to increase. These environments, however, can present challenges for tomosynthesis imaging, since patient movement during the image acquisition sequence is more likely in the ICU (intensive care unit) and clinical setting and can cause difficulties with obtaining the needed series of images.

Thus, it can be appreciated that methods that reduce the number of 2D projection images that are needed for tomosynthesis can help to reduce dosage requirements and can also help to remedy imaging problems related to patient motion.

SUMMARY OF THE INVENTION

It is an object of the present disclosure to advance the art of diagnostic imaging, particularly for tomosynthesis imaging. Embodiments disclosed herein offer methods that can help to reduce the likelihood of artifacts caused by a limited number of projection images that are obtained for tomosynthesis imaging and thus to reduce the amount of exposure needed and the duration of the scanning process.

These and other aspects, objects, features and advantages of the present invention will be more clearly understood and appreciated from a review of the following detailed description of the preferred embodiments and appended claims, and by reference to the accompanying drawings.

According to an embodiment of the present disclosure, there is provided a method for tomosynthesis volume reconstruction comprising: a) acquiring at least a prior projection image of the subject at a first angle and a subsequent projection image of the subject at a second angle; b) generating a synthetic image corresponding to an intermediate angle between the first and second angle by a repeated process of: (i) relating an area of the synthetic image to a prior patch on the prior projection image and to a subsequent patch on the subsequent projection image according to a bidirectional spatial similarity metric, wherein the prior patch and subsequent patch have n×m pixels; (ii) combining image data from the prior patch and the subsequent patch to form a portion of the synthetic image; and c) displaying, storing, processing, or transmitting the generated synthetic image.

BRIEF DESCRIPTION OF THE DRAWINGS

FIG. 1D is a schematic diagram that shows a tomosynthesis apparatus using a plurality of sources.

FIG. 1E is a schematic diagram that shows a portable tomosynthesis imaging apparatus that has its x-ray source mechanically de-coupled from the detector.

DETAILED DESCRIPTION OF THE INVENTION

Figure 1A:
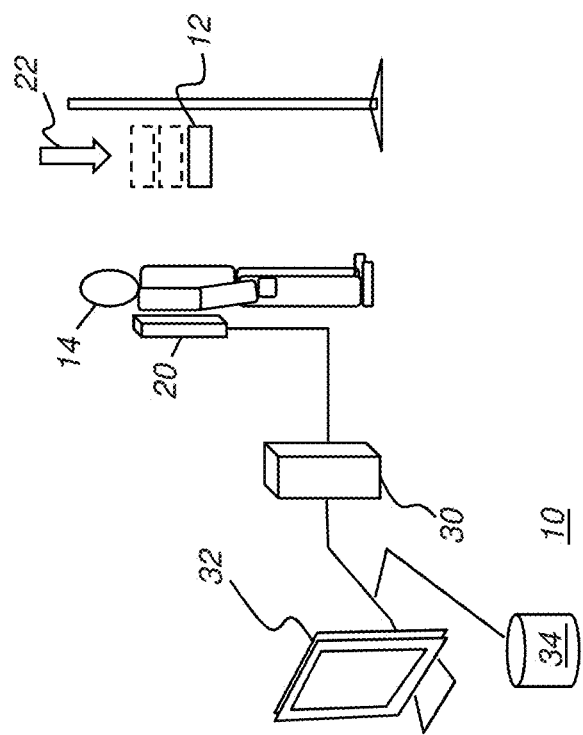
FIG. 1A shows a schematic diagram of a tomosynthesis apparatus.

The following is a detailed description of the preferred embodiments, reference being made to the drawings in which the same reference numerals identify the same elements of structure in each of the several figures.

Where they are used herein, the terms "first", "second", and so on, do not necessarily denote any ordinal, sequential, or priority relation, but are simply used to more clearly distinguish one element or set of elements from another, unless specified otherwise.

In the context of the present disclosure, the terms "viewer", "operator", "viewing practitioner", "observer", and "user" are considered to be equivalent and refer to the viewing practitioner or other person who views and manipulates an x-ray image on a display monitor or other viewing apparatus.

As used herein, the term "energizable" relates to a device or set of components that perform an indicated function upon receiving power and, optionally, upon receiving an enabling signal.

The term "actuable" has its conventional meaning, relating to a device or component that is capable of effecting an action in response to a stimulus, such as in response to an electrical signal, for example.

The term "modality" is a term of art that refers to types of imaging. Modalities for an imaging system may be conventional x-ray radiography, fluoroscopy or pulsed radiography, tomosynthesis, tomography, ultrasound, MRI, or other types of imaging. The term "subject" refers to the patient who is being imaged and, in optical terms, can be considered equivalent to the "object" of the corresponding imaging system.

The term "set", as used herein, refers to a non-empty set, as the concept of a collection of elements or members of a set is widely understood in elementary mathematics. The terms "subset" or "partial subset", unless otherwise explicitly stated, are used herein to refer to a non-empty proper subset, that is, to a subset of the larger set, having one or more members. For a set S, a subset may comprise the complete set S. A "proper subset" of set S, however, is strictly contained in set S and excludes at least one member of set S. A "partition of a set" is a grouping of the set's elements into non-empty subsets so that every element is included in one and only one of the subsets. Two sets are "disjoint" when they have no element in common.

The terms "image" and "image data" can be used interchangeably in the context of the present disclosure. An image that is captured by an imaging apparatus is processed, displayed, transmitted, and stored as image data.

For the image processing steps described herein, the terms "pixels" for picture image data elements, conventionally used with respect 2-D imaging and image display, and "voxels" for volume image data elements, often used with respect to 3-D imaging, can be used interchangeably. It should be noted that the 3-D tomosynthesis image is itself synthesized from image data obtained as pixels on a 2-D sensor array and displays as a 2-D image from some angle of view. Thus, 2-D image processing and image analysis techniques can be applied to the 3-D volume image data. In the description that follows, image processing techniques described as operating upon pixels may alternately be described as operating upon the 3-D voxel data that is stored and represented in the form of 2-D pixel data for display. In the same way, techniques that operate upon voxel data can also be described as operating upon pixels.

With respect to an image detector, the term "pixel" refers to a picture element unit cell containing a photo-conversion circuit and related circuitry for converting incident electromagnetic radiation to an electrical signal.

In the context of the present disclosure, "tomographic imaging" refers to volume radiographic imaging modalities such as computed tomography (CT) or tomosynthesis imaging. Tomographic imaging forms a volume 3-D image of a subject that can be viewed as a planar slice or plane section taken at a specified depth and angle. As noted previously, tomographic imaging obtains 3-D depth information by changing the relative angle between the x-ray source and the subject for each 2-D projection image that is acquired during scanning.

In the context of the present disclosure, the term "depth image" refers to a reconstructed tomographic image that represents depth information obtained from processing multiple 2-D images or projection images of the subject, taken from different angles. Depth images obtained from tomosynthesis do not typically provide full 3-D representation; depth images from computed tomography (CT) provide more complete 3-D depth information. The noun "projection" may be used herein to mean "projection image", referring to one of the 2-D images that is captured and processed to reconstruct a depth image.

In the context of the present disclosure, the term "aspect ratio" has its conventional meaning as related to two-dimensional polygons and other shapes and generally relates height to width in 2-D space. Thus, for example, two squares of different size exhibit the same aspect ratio. Two rectangles may or may not have the same aspect ratio. It should also be noted that a square is considered a special case of rectangular shape with equal sides. Aspect ratios are considered to differ from each other if the ratio between the two varies by more than about 10%, preferably less than 10%.

Reference is made to U.S. Pat. No. 8,139,710 (Jabri et al) and U.S. Pat. No. 7,664,222 (Jabri et al), both of which are incorporated herein in their entirety.

The schematic block diagram of FIG. 1A shows a tomosynthesis imaging apparatus 10 having an x-ray source 12 that directs imaging radiation toward a detector 20 that captures successive images of a subject 14. Detector 20 is in signal communication with a host processor 30, such as an external computer or dedicated processor for example, that processes the obtained data from the tomosynthesis exam session. Processor 30 is in signal communication with a display 32 for displaying the processed, reconstructed volume image. Alternatively, processor 30 can also store the reconstructed volume image content in a memory 34 or transfer this data to another computer or system, for example. To obtain depth information, X-ray source 12 is moved in a linear motion direction 22, shown as a vertical path of travel in the example of FIG. 1A. For a patient in a prone position, X-ray source 12 can be moved in a linear horizontal motion direction.

Figure 1B:
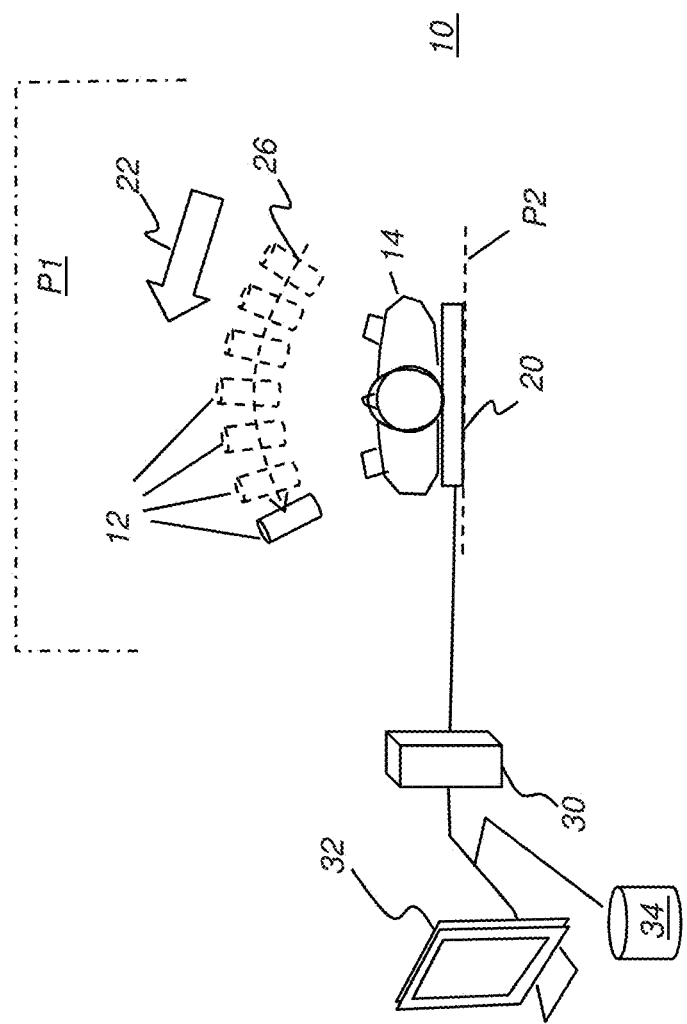
FIG. 1B shows a schematic diagram of a tomosynthesis apparatus using an arcuate travel path for the x-ray source.

Other paths of travel may be non-linear, such as the arcuate path of travel shown for tomosynthesis imaging in the schematic of FIG. 1B. Here, the motion direction 22 is along an arcuate path 26 that is contained in a plane that is orthogonal to the plane P2 of the detector 20. In the view of FIG. 1B arcuate path 26 lies in a plane P1 that is parallel to the plane of the page; plane P2 is orthogonal to the page in this view. In the vertical patient orientation of FIG. 1A and in the horizontal patient orientation of FIG. 1B, including where motion is along a straight line or defines an arc, the motion direction 22 of the x-ray focal spot lies in a plane P1 that is perpendicular to the detector 20.

Figure 1C:
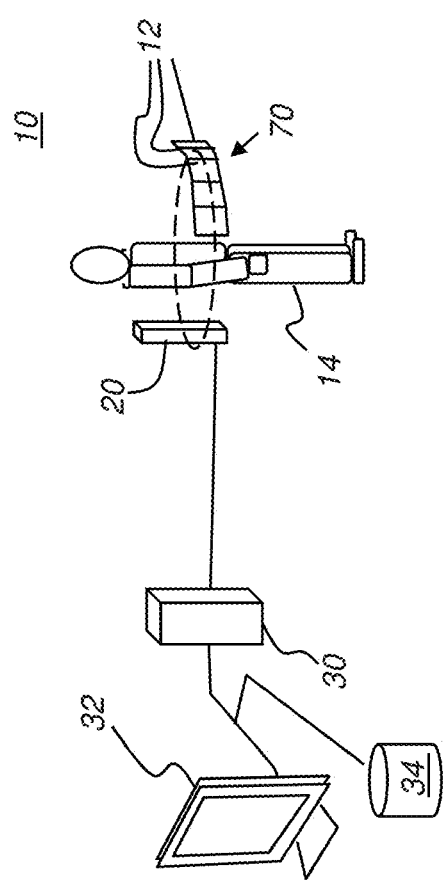
FIG. 1C is a schematic diagram showing a tomosynthesis apparatus using a plurality of sources.

FIG. 1C is a schematic diagram that shows a tomographic imaging apparatus 10 that uses an array 70 of x-ray sources 12. Array 70 may be a carbon nanotube (CNT) array or other array of emitters designed to be fired in sequence in order to change the angle of energy directed through the subject with each acquired 2-D projection image.

FIG. 1D is a schematic diagram that shows a tomosynthesis imaging apparatus 10 another type of array 70 that can be arranged to direct radiation to the patient from different angles. Array 70 can be a CNT array, for example.

FIG. 1E is a schematic diagram that shows a portable tomosynthesis imaging apparatus 100 that has x-ray source 12 mechanically de-coupled from detector 20. A portable transport frame or cart 80 that can be wheeled from one location to another can include a portion of the processing, display, and control logic for image acquisition and processing for subject 14. Apparatus for translating source 12 vertically or over some other path between imaging positions can also be provided by cart 80. Wireless or wired communication can be used for communication with detector 20.

Figure 2A:
FIG. 2A shows an exemplary reconstructed image using sufficient projection images for reconstruction of an image without noticeable ripple artifacts.
Figure 2B:
FIG. 2B shows an exemplary reconstructed image using an insufficient number of projection images for reconstruction of an image and showing noticeable ripple artifacts.

As noted previously in the background section, attempting to reduce the number of projection images used for tomosynthesis reconstruction can lead to view artifacts, such as aliasing and ripple artifacts. By way of illustration, FIGS. 2A and 2B compare tomosynthesis reconstructions with and without a sufficient number of projection images. FIG. 2A shows a slice from an exemplary reconstruction using a sufficient number of projections for reasonable image quality. FIG. 2B shows the same slice from a reconstruction that uses about half of the projection images normally preferred. A view artifact appears that is commonly referred to as a ripple artifact, clearly visible in the reconstructed image of FIG. 2B.

In order to provide suitable image reconstruction without perceptible ripple artifacts, conventional tomosynthesis acquires an ordered set of N projection images, each projection image in the set acquired at one of a corresponding sequence of N capture angles $\alpha$. Except for the first and last image in the set, every projection image n has a corresponding capture angle $\alpha_n$ and is adjacent to a previous projection image (n−1) with corresponding capture angle $\alpha_{n-1}$ and to a subsequent projection image (n+1) with corresponding capture angle $\alpha_{n+1}$. Angular spacing between any two adjacent images in the sequence can be expressed as $\Delta\alpha$.

Embodiments of the present disclosure provide approaches for reducing patient exposure and shortening the scan time by acquiring only a partial percentage of the N projection images that would otherwise be needed to for ripple-free reconstruction. Thus, to obtain an ordered set of projection images that can be used for tomosynthesis, a smaller number of projection images M (with M<N) is acquired, with enlarged angular spacing $\Delta\alpha'$ between adjacent images in the sequence exceeding the $\Delta\alpha$ spacing normally preferred for tomosynthesis without ripple artifacts. The method of the present disclosure then generates, using the acquired images, a subset having a number J≤N of synthetic images. The J synthetic images are generated using projection images that are adjacent to each other in angular sequence. The synthetic images are generated in order to present features at angles that lie between those of adjacent projection images. The method then adds these J synthetic, generated images to supplement the set of M projection images that have actually been acquired, even forming a set of (J+M)≥N images for tomosynthesis reconstruction. Reconstruction can then execute on the combined set of acquired and synthetic images, avoiding artifacts or aliasing that would be otherwise expected with an insufficient number of acquired projection images.

Figure 3A:
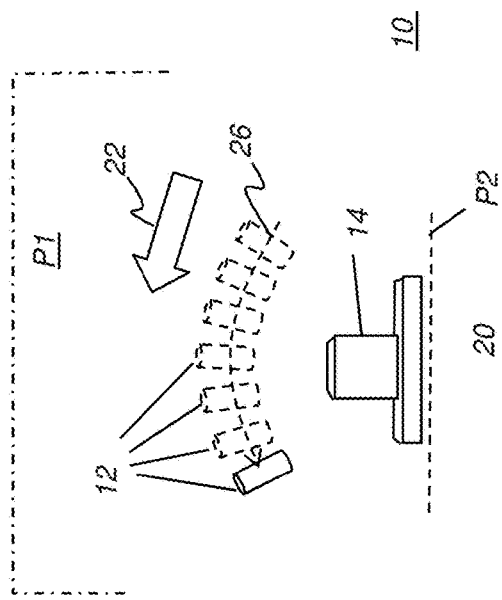
FIG. 3A shows a schematic diagram for imaging a simple geometric subject.
Figure 3B:
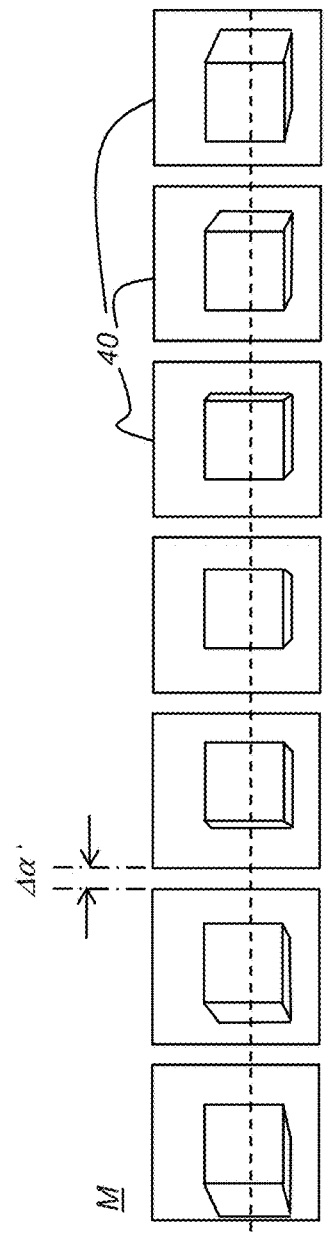
FIG. 3B shows a set of projection images corresponding to the x-ray source positions shown in FIG. 3A.

FIGS. 3A-3D show schematically how embodiments of the present disclosure generate and use synthetic images to supplement acquired projection images for tomosynthesis reconstruction. The schematic diagram of FIG. 3A shows tomosynthesis imaging apparatus 10 acquiring multiple projection images of a geometric object as subject 14. Because each projection image is taken from a different angular position, the projection images reflect the subject's depth information. As X-ray source 12 is translated over arcuate path 26, as noted previously, the detector 20 acquires a series of M projection images with source 12 positioned at regular angular increments Δα. FIG. 3B shows the ordered set of M (here M=7) projection images 40 captured using detector 20, arranged in right-to-left sequence to correspond to the right-to-left arcuate movement shown in FIG. 3A. Each projection image has an associated capture angle α. An enlarged angular spacing Δα' is used for set M.

Figure 3C:
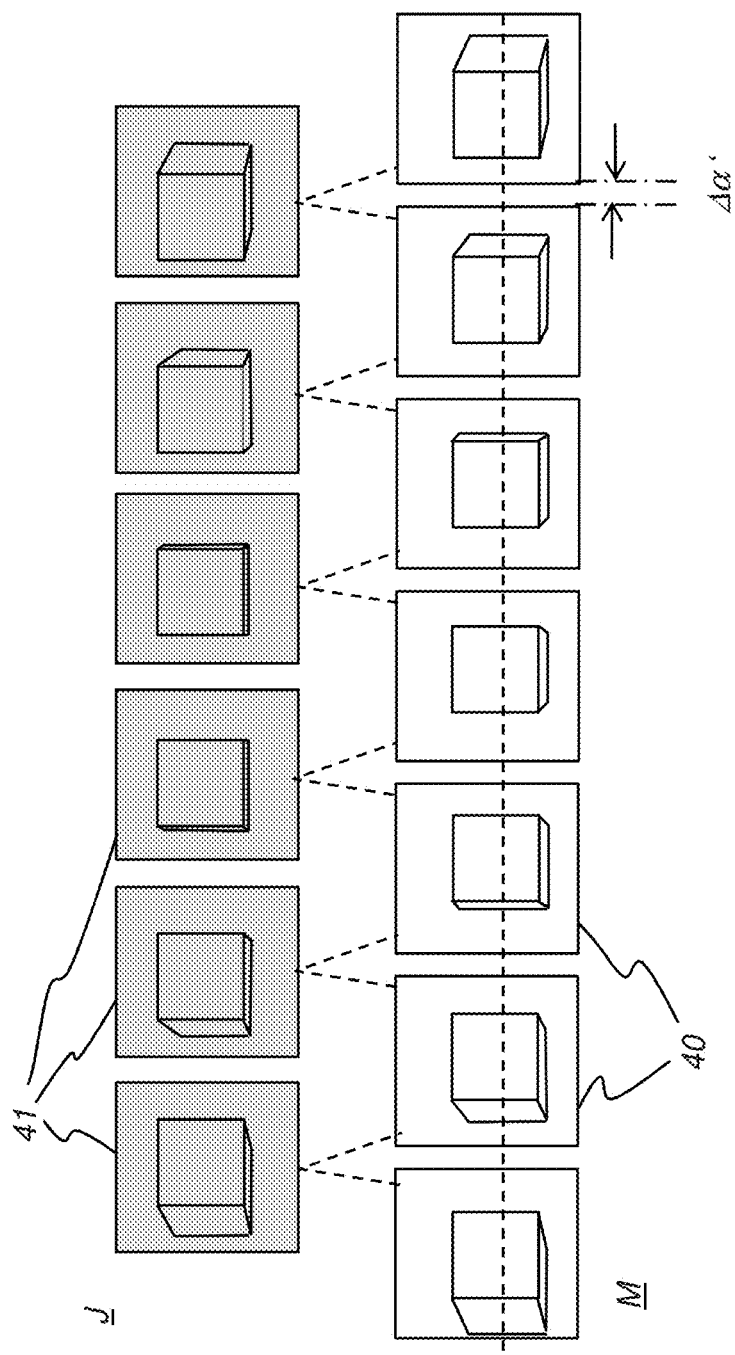
FIG. 3C shows generation of a number of synthesized images.

FIG. 3C shows generation of a subset J (here J=6) of synthetically generated images 41 that can be added to the acquired projection images 40 of set M. As shown in FIG. 3C, each of synthetically generated images 41 is formed to be intermediate two acquired projection images 40. Data from two adjacent projection images 40 is used to form synthetically generated images 41, as described in more detail subsequently.

Figure 3D:
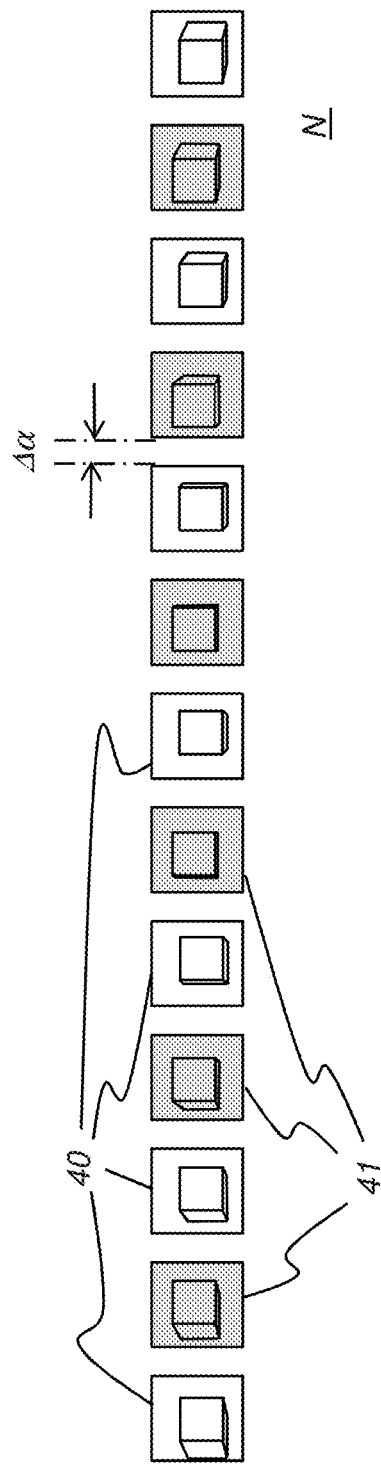
FIG. 3D shows combining the synthesized images with the acquired real projection images.

FIG. 3D shows how the synthetically generated images 41 supplement the acquired projection images 40 to provide a set N of images that can be used for tomosynthesis reconstruction. Images 41 are synthetically formed at angles lying between the angles used for acquired projection images 40. As is suggested in FIGS. 3A-3D, the depth information is preserved in the synthetically generated images 41. The effective angular increment for the assembled set N as shown in FIG. 3D is Δα as described above.

Figure 4:
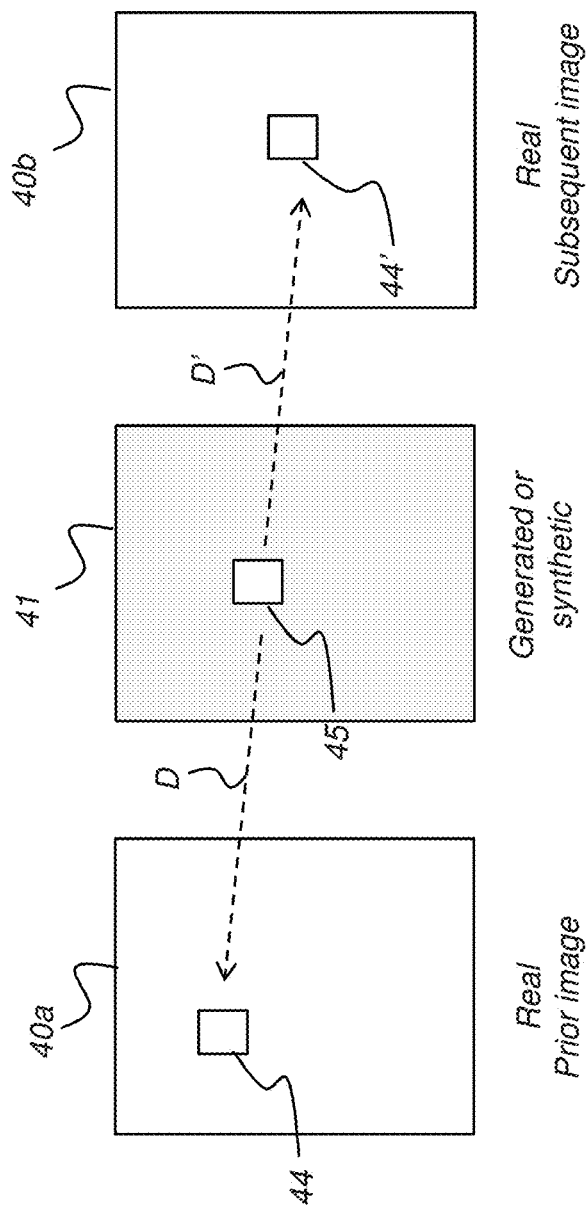
FIG. 4 is a schematic diagram that shows generation of a synthetic image according to a motion vector.

The schematic view of FIG. 4 shows a method of view interpolation using bidirectional spatial similarity. The method generates a synthetic image 41 according to image content from two real projection images that are acquired in a tomosynthesis scan. One of the acquired projection images is termed the prior image 40a, acquired at an earlier point in the tomosynthesis scan from the second projection image, termed a subsequent image 40b. Each acquired projection image 40 has an associated angle α, according to the acquisition sequence, as described previously. The prior image and the subsequent images can be adjacent in the series of acquired images.

Synthetic image 41 can be considered as a set of patches 45, arranged in mosaic fashion, wherein each patch has a set of n×m pixels. The patch location coordinates within an image can be identified according to a pixel offset, such as by the number of pixels offset from the upper left hand corner of the image to the upper left hand corner of the patch, for example. Patch 45 in the generated synthetic image 41 is identified and positioned according to searches about a region of the respective prior and subsequent acquired images at about the same relative coordinate location.

As shown in FIG. 4, a patch 44 in the search area of the prior acquired image 40a has a vector, the prior vector D, from the upper left hand corner of the synthetically generated patch 45 to the prior image patch 44. There is a corresponding patch 44' in the subsequent image 40b where the upper left hand corner is pointed by the negative vector D' of prior vector D. The two patches 44 and 44' can be compared by some spatial similarity metric, e.g., sum of squared differences (SSD) of the pixels of the two patches. This metric can be similarly computed for each pair of patches in the search area. Two corresponding patches 44 and 44' having an optimum value, e.g. a minimum for the SSD case, are selected and combined to form the patch 45 for the synthetically generated image.

Figure 5:
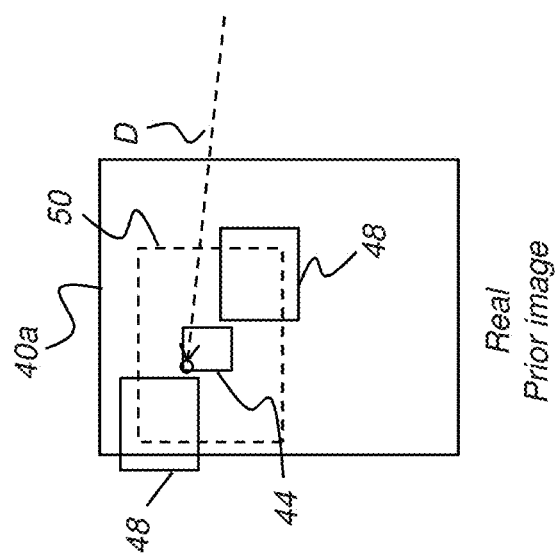
FIG. 5 is a schematic diagram showing search and matching structures according to an embodiment of the present disclosure.

In a search routine, as shown in FIGS. 4 and 5, a patch 44 having a given position is identified on the prior image 40a. The processing logic searches for the same patch 44' on subsequent projection image 40b. The dashed arrows indicate prior vector D and negative vector D' for relative translation of patch 44 between prior and subsequent images 40a, 40b. An estimate is calculated for positioning synthesized patch 45 within an intermediate image, synthetic image 41. Techniques for calculating the new position for the designated patch 44 take into account the amount of translation indicated between prior and subsequent images 40a, 40b, along with angular transformation, and identify a suitable position according to this analysis. The logic described for patch 44 is repeated for similar blocks of projection images 40a and 40b, assembling synthetic image 41 one block at a time. Patch 45 in synthetic image 41 can be, for example, a weighted average of patches 44 and 44' or may simply copy the patch 44 or 44' that provides the best match, with some adjustment for angular difference, since accurate representation of the patch area needs to take angular transformation into account for each patch for synthetic image 41 between prior and subsequent images 40a and 40b. Thus, for example, a square n×m patch where n=m from the prior image may or may not have exactly the same n×m dimensions in the subsequent image, since both prior and subsequent images are not obtained with the source and detector at the same relative angle.

According to an embodiment, bidirectional interpolation can be used to locate patch 44 within generated image 41. Forward or reverse translation in either direction with respect to prior vector D can be used to describe the translation of image content between the separate images.

An embodiment of the present disclosure improves upon results obtained using ordinary bidirectional interpolation for mapping the spatial changes relating to each patch 44. The schematic diagram of FIG. 5 shows structures used for view interpolation according to an embodiment. A search region or window 50 is defined based on the predicted translation of patch 44 from one image to the next in sequence, according to prior vector D and according to the associated angle of image acquisition. Prior vector D is established according to the relationship of the path of the x-ray source 12 relative to the detector 20, as described previously with relation to FIG. 1B, for example. That is, based on the geometry of the tomosynthesis scanning apparatus, the basic direction of prior vector D can be approximated with respect to any patch 44 of the image. This a priori knowledge of scanning motion and angular increments helps to define the approximate bounds of search window 50. One or more match windows 48 can then be defined, at least predominantly within search window 50.

One known problem with bidirectional interpolation relates to blocking artifacts, in which boundaries between blocks can be readily observed at various positions throughout the reconstructed synthetic image. The Applicants have found that this artifact problem relates to the fact that basic bidirectional interpolation uses only a block matching energy term:

$$c(u, v) = \sum_{(x,y) \in S(B)} |f_{prior}(x - u, y - v) - f_{subsequent}(x + u, y + v)| \quad (1)$$

$$(u^*, v^*) = \arg \min c(u, v) \quad (2)$$

$$f(x, y) = \quad (3)$$
$$0.5 \times (f_{prior}(x - u^*, y - v^*) + f_{subsequent}(x + u^*, y + v^*)) \ (x, y) \in S(B)$$

wherein S(B) is the search region, approximated by search window 50 in the example of FIG. 5.

Figure 6:
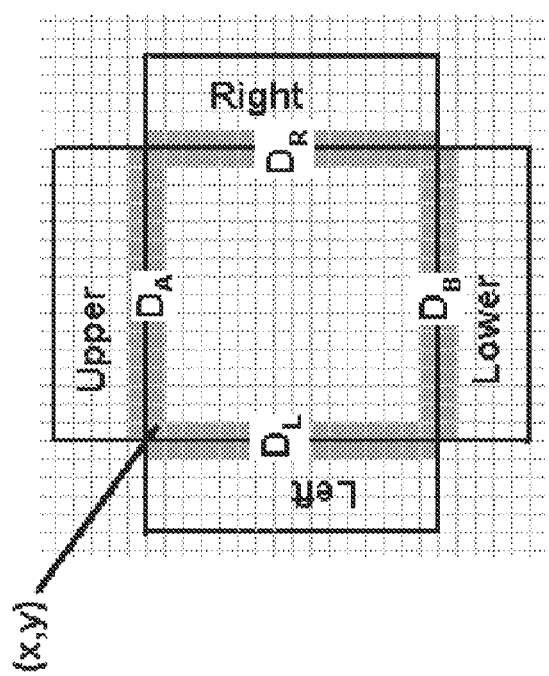
FIG. 6 is a schematic diagram showing boundary matching.

To help mitigate blocking artifacts, the Applicants use an improved spatial similarity metric, formed by adding terms that encourage spatial correlation with neighboring patches. This includes two types of terms: a boundary matching energy and a flow field smoothing energy. FIG. 6 shows the meaning of boundary matching terms used herein.

The basic energy relationship E can be expressed as follows:

$$E = \text{block matching energy} + \text{boundary matching energy} + \text{flow field smoothing energy} \quad (4)$$

Block matching energy can then be formulated as follows:

$$E_{blockmatching} = \sum_{(x,y) \in S(B)} |f_{left}(x - u, y - v) - f_{right}(x + u, y + v)| \quad (5)$$

A flow field term expresses the consistency of flow direction:

$$E_{flow\ field} = \sum_{i \in neighbors} |(u - u_i)| + |(v - v_i)| \quad (6)$$

where, as shown in FIG. 6:

$$\text{neighbors} = \{\text{upper, lower, left, right}\} \quad (7)$$

$$E_{boundary\ matching} = D_A + D_B + D_L + D_R \quad (8)$$

$$D_A(u, v) = \quad (9)$$

$$\sum_{x=0}^{N-1} |0.5(f_{left}(x - u, y - v) - f_{right}(x + u, y + v)) - f^{k-1}(x, y - 1)|$$

Figure 7:
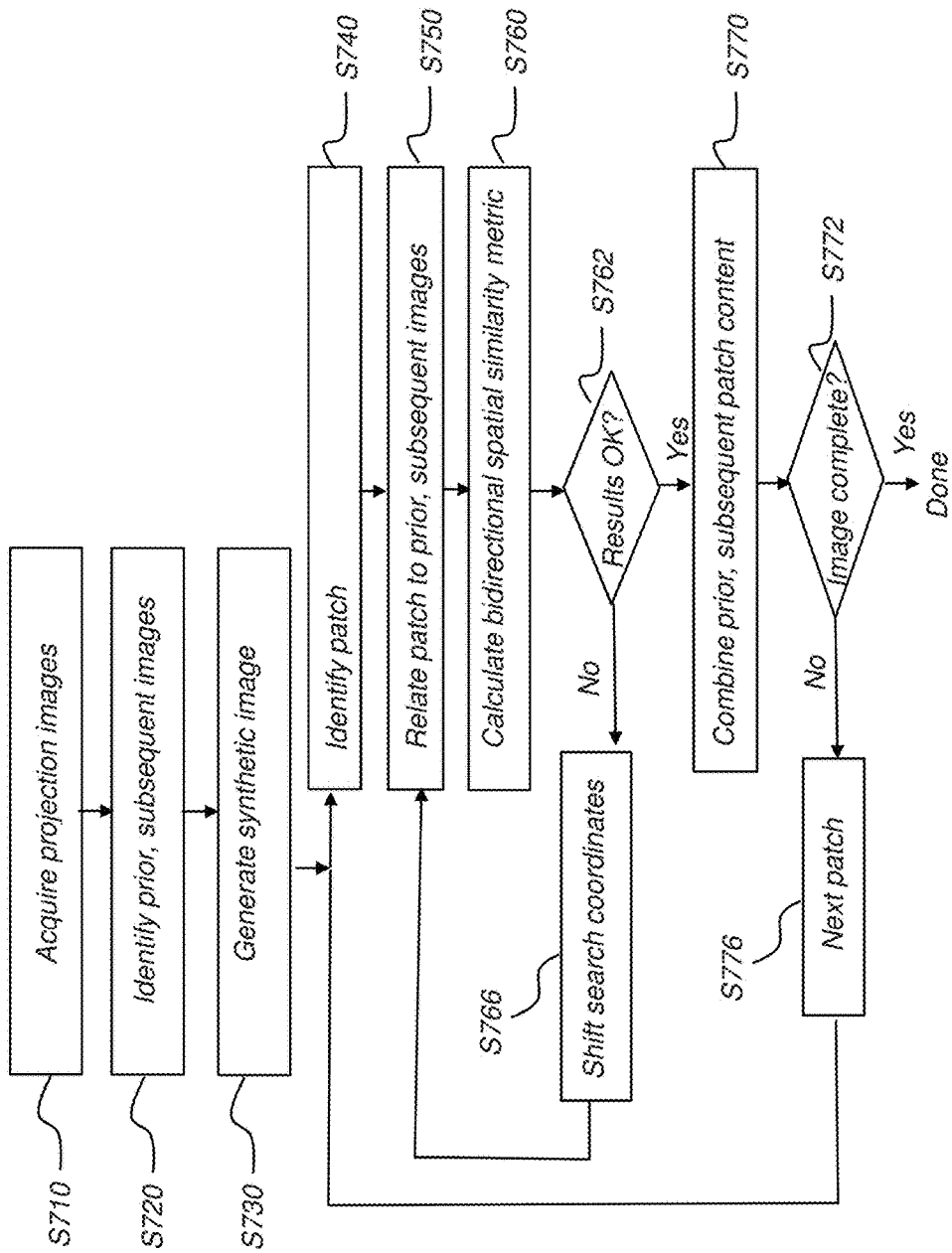
FIG. 7 is a logic flow diagram showing a method for tomosynthesis reconstruction using a synthetic image according to an embodiment of the present disclosure.

The logic flow diagram of FIG. 7 shows a method for tomosynthesis reconstruction using a synthetic image according to an embodiment of the present disclosure. In an acquisition step S710, the projection images are acquired from the tomosynthesis scan, as described previously. In an image identification step S720, prior and subsequent images are identified. In a synthetic image generation step S730, the synthetic image is generated, using the steps that follow. A patch identification step S740 identifies a patch for the synthetic image. A patch matching step S750 then performs the search and matching processes described previously with respect to FIGS. 4 and 5. A similarity calculation step S760 then performs the calculation for patch matching using the bidirectional spatial similarity metric described previously. A decision step S762 then determines whether or not the energy calculations are optimized for the patch. If not, a shift step S766 adjusts the patch location within the search area and returns to step S750. If an optimum match is achieved, a combination step S770 then combines the prior and subsequent patch content for the synthetic image. A decision step S772 then determines whether or not the synthetic image is complete or whether another patch is to be added with a patch increment step S776 that selects the next patch location and returns to step S740.

Figure 8B:
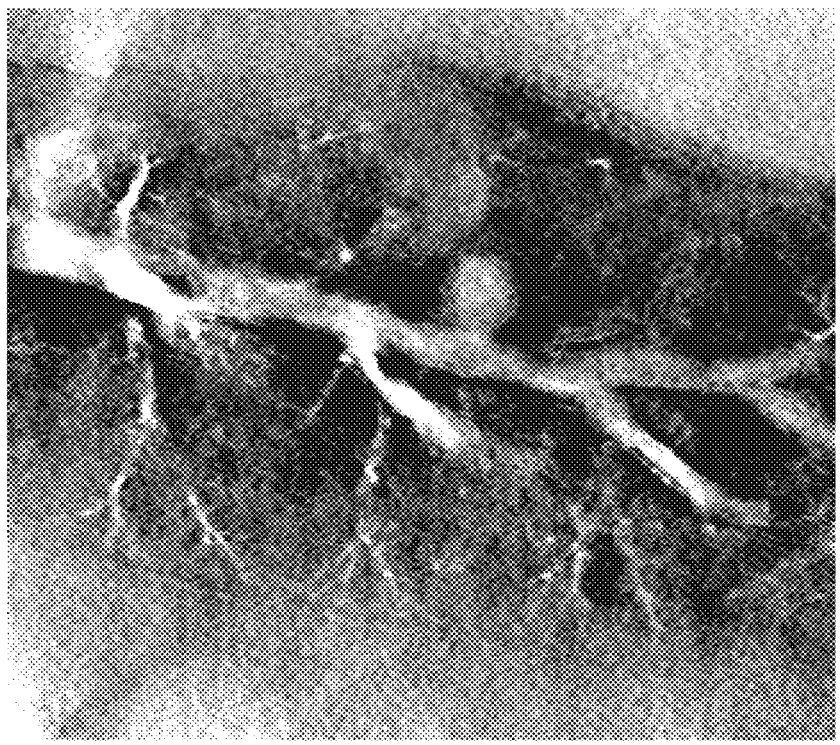
FIG. 8B shows the improved results for the FIG. 8A image with combined projection and synthesized images according to an embodiment of the present disclosure.
Figure 8A:
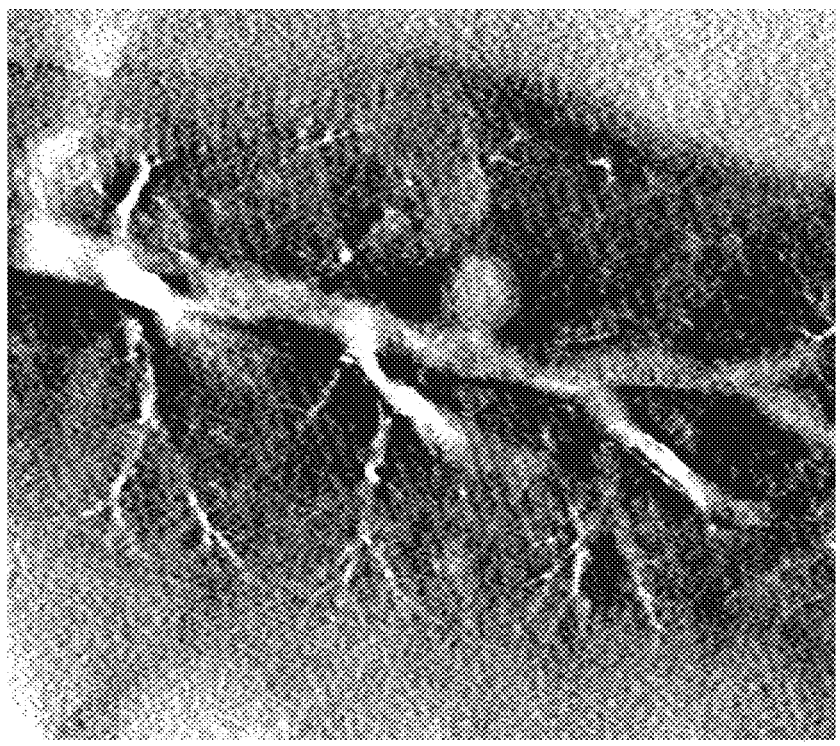
FIG. 8A shows an exemplary tomosynthesis image reconstructed from a number of projection images.

Embodiments of the present disclosure show improvement over earlier interpolation methods, particularly with respect to reduction of ripple and related view artifacts. FIG. 8A shows an exemplary tomosynthesis image reconstructed from 30 projection images. FIG. 8B shows the improved results obtained by combining the acquired projection images with 29 generated images formed as described herein. Ripple artifacts are substantially eliminated in the improved version.

Consistent with one embodiment, the present invention utilizes a computer program with stored instructions that control system functions for image acquisition and image data processing for image data that is stored and accessed from an electronic memory. As can be appreciated by those skilled in the image processing arts, a computer program of an embodiment of the present invention can be utilized by a suitable, general-purpose computer system, such as a personal computer or workstation that acts as an image processor, when provided with a suitable software program so that the processor operates to acquire, process, transmit, store, and display data as described herein. Many other types of computer systems architectures can be used to execute the computer program of the present invention, including an arrangement of networked processors, for example.

The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the image data processing arts will further readily recognize that the equivalent of such a computer program product may also be constructed in hardware.

It is noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It is understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A method for tomosynthesis volume reconstruction, comprising:
    identifying a number N of projection images of a subject for the tomosynthesis volume reconstruction, the number N of projection images corresponding to an angular spacing $\Delta\alpha$;
    identifying an enlarged angular spacing $\Delta\alpha'$, wherein $\Delta\alpha' > \Delta\alpha$;
    using a predetermined scanning geometry, sequentially acquiring a set of M prior projection images of the subject at a first angle and subsequent projection images of the subject at a second angle, where 2<M<N, where the first angle is spaced from the second angle by the enlarged angular spacing $\Delta\alpha'$;
    using the set of M prior and subsequent projection images, generating a set of J synthetic images corresponding to an intermediate angle between the respective first and second angle, where J<M and (J+M)≥N, by a repeated process of:
        (i) selecting a constrained region in the prior projection image based on the predetermined scanning geometry;
        (ii) identifying a first vector that extends in a first direction from a first patch coordinate of the synthetic image to a prior patch coordinate in the prior projection image, the prior patch coordinate being in the prior projection image within the constrained region;
        (iii) searching a region of the subsequent projection image according to a second vector extending in a second direction, opposite the first direction, from the first patch coordinate of the synthetic image to the subsequent projection image;
        (iv) identifying a subsequent patch according to a bidirectional spatial similarity metric between the prior patch and a corresponding subsequent patch; and
        (v) forming the synthetic image by combining the image data from the prior and subsequent patches; and
    displaying, storing, processing, or transmitting the generated synthetic image.

2. The method of claim 1 further comprising reconstructing the tomosynthesis volume using the set of M prior and subsequent acquired projection images and the set of J generated synthetic images, where 2<M<N, where J<M, and where (J+M)≥N.

3. The method of claim 2 further comprising displaying a portion of the reconstructed tomosynthesis volume.

4. The method of claim 1 wherein the bidirectional spatial similarity metric computes a block matching energy for the prior patch and subsequent patch.

5. The method of claim 1 wherein the bidirectional spatial similarity metric computes a boundary matching energy for the prior patch and subsequent patch.

6. The method of claim 1 wherein the bidirectional spatial similarity metric computes a flow field smoothing energy between the prior patch and subsequent patch.

7. The method of claim 1 wherein combining the image data comprises computing an average between a data value of the prior patch and a corresponding data value of the subsequent patch.

8. A method for tomosynthesis volume reconstruction, comprising:
    a) identifying a number N of projection images of a subject to provide a ripple-free tomosynthesis volume reconstruction, the number N of projection images corresponding to an angular spacing $\Delta\alpha$;
    b) identifying an enlarged angular spacing $\Delta\alpha'$, wherein $\Delta\alpha' > \Delta\alpha$;
    c) using a predetermined scanning geometry, sequentially acquiring a set of M successive projection images of the subject, each image at a corresponding acquisition angle of an x-ray source relative to a detector spaced at the enlarged angular spacing $\Delta\alpha'$, where 2<M<N;
    d) generating a set of J synthetic images, where J<M, where (J+M)≥N, where each synthetic image corresponds to an intermediate angle between respective successive projection images, by a repeated process of:
        selecting a constrained region in a prior projection image of set M based op the predetermined scanning geometry;
        identifying, in the prior image within the constrained region, a block of a projection image acquired at a first acquisition angle;
        determining a vector for the identified block of the prior image by matching the block in a subsequent image of set M acquired at a second acquisition angle;
        computing a block matching energy for the block corresponding to the prior and subsequent images;
        computing a boundary matching energy for the block that encourages matching of boundaries of the block between the prior and subsequent images;
        computing a flow field smoothing energy according to the vector; and
        adding the block to the synthetic image corresponding to the enlarged angular spacing $\Delta\alpha'$ between the first and second acquisition angles;
    e) reconstructing the tomosynthesis volume using the set of M projection images and the set of J synthetic images; and
    f) displaying, storing, or transmitting at least a portion of the reconstructed tomosynthesis volume.

9. The method of claim 8 wherein acquiring the set of projection images comprises obtaining image data wherein the radiography detector is mechanically de-coupled from the x-ray source.

10. A method of operating a radiographic tomosynthesis imaging system having an x-ray source and a digital radiographic detector, the radiographic tomosynthesis imaging system configured to reconstruct a three dimensional (3D) radiographic image of an object from at least N two dimensional (2D) radiographic projection images of the object, the method comprising the steps of:
    revolving the x-ray source along an arc about the object and capturing a sequence of M 2D radiographic projection images of the object in the digital radiographic detector, wherein the sequence of M 2D radiographic projection images of the object each comprise radiographic image data of the object captured at regularly spaced angular positions of the x-ray source separated by an angle $\Delta\alpha'$, and wherein M<N;

generating J synthetic radiographic images of the object using only the captured sequence of M 2D radiographic projection images of the object, wherein J<M and J+M≥N, the J synthetic radiographic images of the object each approximate a 2D radiographic image of the object as if captured at an angular position of the x-ray source between a prior image and a subsequent image in each pair of the captured sequence of M 2D radiographic projection images, the J synthetic radiographic images of the object each approximate a 2D radiographic image of the object as if captured at a regularly spaced angular position of the x-ray source separated by an angle $\Delta\alpha$ from the prior image in the captured sequence of M 2D radiographic projection images of the object and separated by the angle $\Delta\alpha$ from the subsequent image in the captured sequence of M 2D radiographic projection images of the object, and wherein $\Delta\alpha<\Delta\alpha'$; and reconstructing a 3D radiographic image of the object using only the captured sequence of M 2D radiographic projection images of the object and the J synthetic radiographic images of the object.

11. The method of claim 10, further comprising displaying a portion of the reconstructed 3D radiographic image of the object.

12. The method of claim 10, wherein the step of generating J synthetic radiographic images comprises:

selecting a first subset of image data contained in the prior image of the captured sequence of M 2D radiographic projection images, the first subset of the image data comprising an array of n×m adjacent image pixels;

determining a first vector from a pixel in the first subset of the image data contained in the prior image of the captured sequence of M 2D radiographic projection images to a corresponding pixel of the synthetic image separated by the angle $\Delta\alpha$ from the prior image of the captured sequence of M 2D radiographic projection images;

determining a second vector from a pixel in a subset of the image data contained in the subsequent image of the captured sequence of M 2D radiographic projection images to the corresponding pixel of the synthetic image, the synthetic image is separated by the angle $\Delta\alpha$ from the subsequent image of the captured sequence of M 2D radiographic projection images, and wherein the second vector is a negative of the first vector;

selecting a second subset of image data contained in the subsequent image of the captured sequence of M 2D radiographic projection images, the second subset of the image data comprising an array of n×m adjacent image pixels determined by the second vector pointing to the pixel in the subset of the image data contained in the subsequent image;

combining the first subset of the image data contained in the prior image and the second subset of image data contained in the subsequent image to generate a subset of image data of the synthetic image separated by the angle $\Delta\alpha$ from the prior image, including generating the corresponding pixel of the synthetic image; and displaying, storing, processing, or transmitting the generated subset of image data of the synthetic image.

13. The method of claim 12, further comprising computing a block matching energy for the first subset of image data and the second subset of image data.

14. The method of claim 12, further comprising computing a boundary matching energy for the first subset of image data and the second subset of image data.

15. The method of claim 12, further comprising computing a flow field smoothing energy between the first subset of image data and the second subset of image data.

16. The method of claim 12, further comprising computing the first vector that extends in a first direction from a first coordinate of the synthetic image and computing the second vector that extends in an opposite direction from the first coordinate of the synthetic image to the subsequent image.

17. The method of claim 12, wherein the steps of selecting a first subset of the image data and selecting the second subset of the image data comprises defining a constrained search region for relating an area of the synthetic image to the first subset of the image data in the prior image and to the second subset of the image data in the subsequent image.

18. The method of claim 12, wherein the step of combining the subsets of image data comprises computing an average between a data value of the first subset of the image data and a corresponding data value of the second subset of the image data.

* * * * *